United States Patent [19]
Maxwell, III

[11] Patent Number: 5,925,036
[45] Date of Patent: Jul. 20, 1999

[54] APPARATUS FOR REPAIRING BONE STRUCTURE USING LASER

[76] Inventor: Ralph Maxwell, III, 1705 S. Morrison, P.O. Drawer 3028, Hammond, La. 70404

[21] Appl. No.: 08/934,610

[22] Filed: Sep. 22, 1997

[51] Int. Cl.⁶ .............................. A61B 17/36; A61B 1/00
[52] U.S. Cl. ............................................... 606/13; 606/14
[58] Field of Search .................. 606/10, 11, 12, 606/13, 14, 15, 16, 17, 32, 44, 45; 600/104, 105, 106, 107, 108

[56] References Cited

U.S. PATENT DOCUMENTS

| | | |
|---|---|---|
| 4,718,406 | 1/1988 | Bregman et al. |
| 4,846,171 | 7/1989 | Kauphusman et al. ..................... 606/15 |
| 5,027,792 | 7/1991 | Meyer ...................................... 600/104 |
| 5,186,714 | 2/1993 | Boudreault et al. ....................... 604/21 |
| 5,290,279 | 3/1994 | Bonati et al. .............................. 606/15 |
| 5,293,872 | 3/1994 | Alfano et al. ............................. 606/15 |
| 5,333,603 | 8/1994 | Schuman ................................. 600/108 |
| 5,437,661 | 8/1995 | Rieser ...................................... 606/15 |
| 5,441,498 | 8/1995 | Perkins .................................... 606/15 |

*Primary Examiner*—Linda C. M. Dvorak
*Assistant Examiner*—Sonya C Harris
*Attorney, Agent, or Firm*—Keaty & Keaty

[57] ABSTRACT

The invention relates to a medical instrument and more particularly to a system for repairing damaged bone structure. A hand-held instrument is formed with a plurality of channels allowing connection of the instrument to a source of laser beam, to a television monitor, to a vacuum suction tube, to a connector for delivering medication or bone sealant to the treatment area. A foot pedal allows a dentist or physician to control delivery of the electrical, mechanical, and vacuum forces to the damaged area, as well as examine and monitor the treatment procedure on a television monitor.

5 Claims, 7 Drawing Sheets

APPARATUS FOR REPAIRING BONE STRUCTURE USING LASER

BACKGROUND OF THE INVENTION

The present invention relates to medical technology, and more particularly to an apparatus adapted for use when conducting minor surgeries on a patient with laser.

Conventionally, during invasive procedures, a doctor needs to determine the extent of damage existing in a bone structure of a patient. The examination is usually conducted with a low-powered optical device or even without any assistance from optical devices. The difficulty in a thorough examination is further complicated if an emergency patient is delivered to a medical facility not equipped with sophisticated medical equipment.

Additionally, some of the medical procedures, for example dental procedure in removing caries is conducted at a dentist's office with the dentist using his eyesight to detect damage to the teeth or bone structure of the patient. In recent years, various improvements have been achieved with regards to performing conventional dental procedures, such as removal of caries and filling of teeth. Laser technology has been incorporated into the tools for treatment of caries and periodontal diseases. Laser drills have been tested in place of conventional dental drills for eliminating the decay that causes small cavities. Laser technology has also been approved by the Federal Drug Administration for surgery on soft tissue, such as gum surgery for periodontal disease.

When using lasers, great care should be exercised in properly aiming the beam to the repair cite, so as to avoid damage to other parts of the bone structure or soft tissue. Even though heat from the laser is better absorbed by the decay than the solid enamel-covered teeth, still caution must be exercised when operating with a laser instrument. Dentists who are qualified to practice laser dentistry usually undergo many hours of training and are considered specialists in highly specialized equipment.

It has been observed that the use of laser eliminates pain and allows to form smaller incisions in the soft tissue of the patient, since a laser beam can be precisely pinpointed to the area that needs treatment. Still, the need remains for a tool that will allow to inspect the cite of injury or damage prior to using a laser. The present invention contemplates provision of a medical apparatus that can be used for various treatment procedures, particularly adapted for treatment of a damaged bone structure of the patient.

SUMMARY OF THE INVENTION

It is an object of the present invention to provide an apparatus for repairing bone structure using laser.

It is another object of the present invention to provide an apparatus suitable for use in a variety of medical procedures involving different areas of a patient's body.

It is a further object of the present invention to provide a medical device that can be utilized for treatment of patients both in the hospital and on an outpatient basis.

These and other objects of the present invention are achieved through a provision of an apparatus for repairing the damaged bone structure which comprises a hand-held instrument having a generally cylindrical body with a plurality of channels formed in the body. One of the channels retains a television fiber optic cable that delivers light of different colors and intensity to the damaged site an is operationally connected to a television monitor to allow a treating physician to inspect the damaged bone tissue.

A second channel houses a laser cable for delivering a laser beam through the hand-held instrument and allowing to make a skin incision and then painless incision into the bony tissue of the patient, then penetrate the tip of the hand-held instrument close to the damaged area. The third channel formed in the body houses, in one of the embodiments, a monofilament cleaner that can be selectively extended through an open distal end of the instrument body and separate the damaged tissue from the remainder of the bone structure when a rotational force is imparted on the monofilament cleaner. The cleaner is connected to an external source of rotational power, forcing the cleaner to move at high speeds and break away the damaged tissue.

The fourth of said channels is fluidly connected to a source of liquid, for example, hydrogen peroxide, water or other means for irrigating the site and stopping bleeding. Still another of the channels is adapted for connection to a vacuum source to establish a suction force through the body of the instrument and remove the separated tissue, blood, clots, and fluids from the treatment site.

The exterior of the instrument body carries two or more normally closed pin connectors. One of the connectors can be connected to the vacuum suction line, while the second connector is adapted for attachment to a syringe holding medication, bone sealant, dental cavity filler and other suitable containers for delivering the treatment medication to the damaged area.

A control pad, such as a foot pedal is provided for connecting the hand-held instrument to a variety of external devices. One of the switches mounted on the control pad allows to control direction of the tip of the fiber optic light source cable for proper examination of the injured site. Other control knobs allow to deliver a desired color and intensity light beam through the fiber optic cable. Still another switch allows to control operation of the television monitor and magnify the site of the injury viewed on the television screen.

Other switches mounted on the control pad allow to operationally connect the hand-held instrument to a source of fluid, such as water for irrigation of the damaged site, to a vacuum creating motor, and to a rotational motor that transmits torque to the monofilament cleaner. Alternatively, when a bi-polar cautery is used for burning away the damaged tissue, this motor can be substituted by an electrical current generator.

The exterior of the instrument body carries two manual switches. One of the switches moves the fiber optic cable in and out of the body, while the second switch allows to move the monofilament cleaner or the bi-polar cautery in and out of the instrument body. Microforceps could be extended through tool for removal of bone foreign bodies.

Provision of the various cables and conduits in the instrument body allows to expeditiously conduct an exploratory and treatment procedure on dental patients, perform orthopedic repair procedure, perform a spinal surgery or neurosurgery.

BRIEF DESCRIPTION OF THE DRAWINGS

Reference will now be made to the drawings, wherein like parts are designated by like numerals, and wherein.

DETAILED DESCRIPTION OF THE PREFERRED EMBODIMENT

Figures 1, 4:
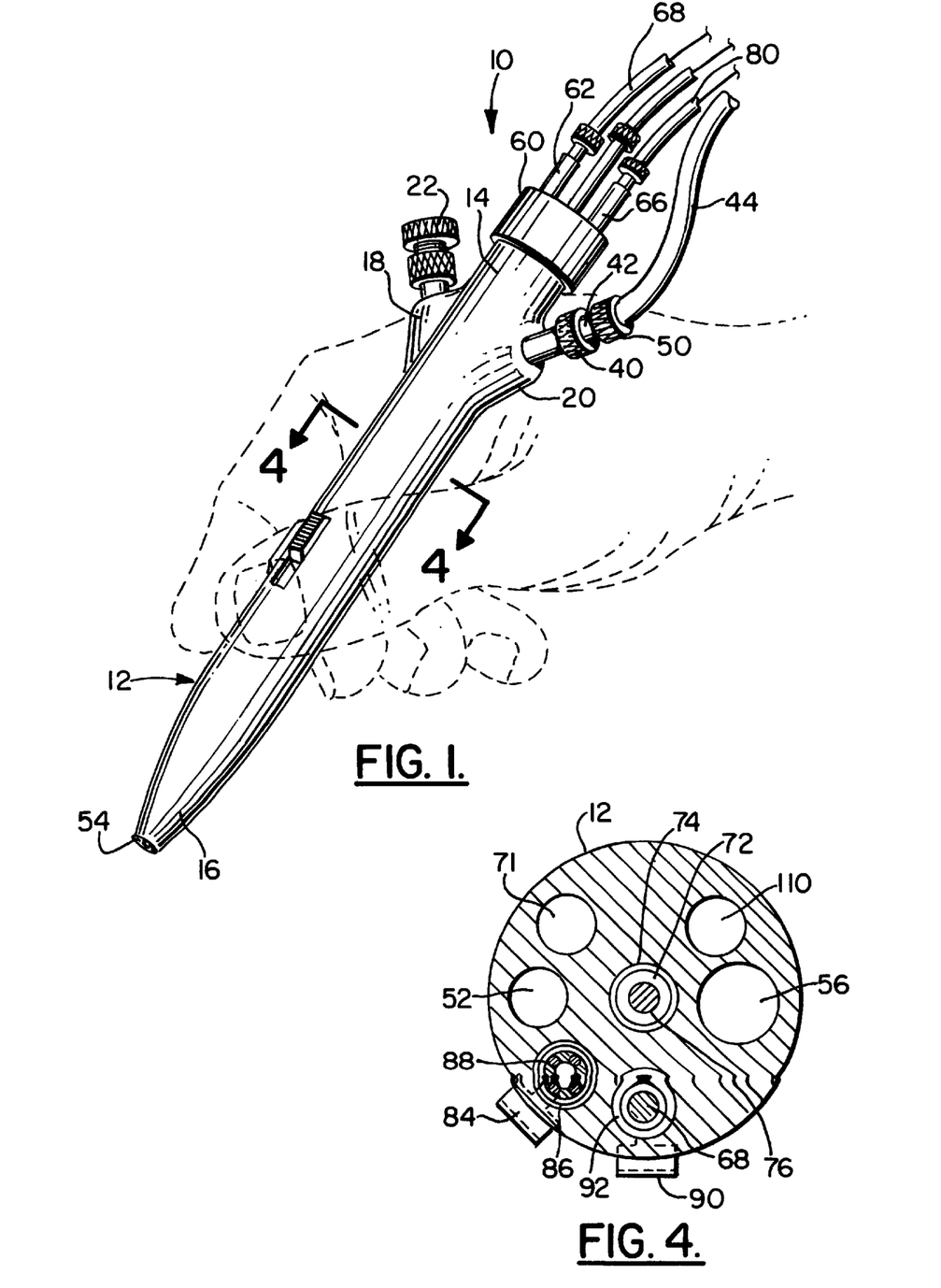
FIG. 1 is a perspective view of a hand-held medical instrument in accordance with the present invention.
FIG. 4 is a cross-sectional view taken along lines 4—4 of FIG. 1.

Turning now to the drawings in more detail, numeral 10 designates the handheld medical tool in accordance with the present invention. The tool 10 comprises an elongated tubular body 12 having a proximal end 14 and a distal end 16. An enlargement 18 is formed adjacent the proximate end 14, and a second enlargement 20 is formed on a diametrically opposite side of the body 12 adjacent the proximate end 14.

The first enlarged portion 18 is formed with a normally closed opening with a two-part plug 22. The plug 22 is comprised of a first plug member 24 (FIG. 2) permanently secured in the enlargement member 18 and a second removable plug member 26 (FIG. 2) threadably engageable with an internal threaded opening (not shown) formed in the free end of the plug member 24.

The plug member 24 is provided with a through axial opening (not shown) extending in co-alignment with an aperture 28 formed in the first enlargement portion 18. The plug member 26 normally closes the access to the opening 28 through a threaded engagement with a plug member 24. The plug member 26 has a solid cap 30 which prevents communication between the aperture 28 and exterior of the tool 10.

Figures 2, 3:
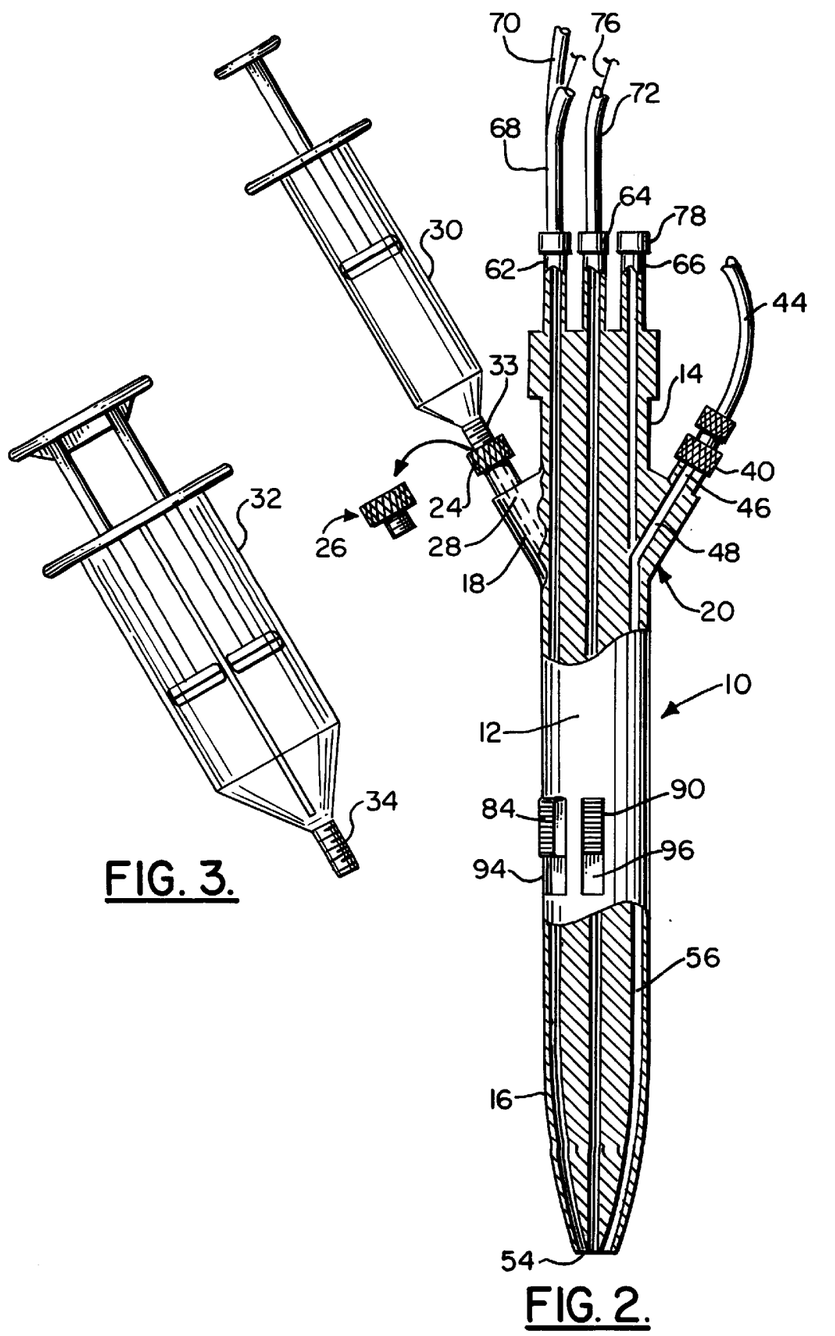
FIG. 2 is a perspective, partially sectional view of the instrument shown in FIG. 1, in use with a syringe delivering fluids to a treatment cite.
FIG. 3 is a perspective view of a two-plunger syringe used with the instrument shown in FIGS. 1 and 2.

A syringe 30 having a threaded nose portion 32 is adapted for engagement with the plug member 24, as shown in FIG. 2, for the purposes that will be described in more detail hereinafter. The syringe 30 can be a conventional one-plunger syringe, or a multi-plunger syringe 32, as shown in FIG. 3. The syringes 30 and 32 have openings (not shown) formed in the nose portions 32 and 34, respectively. When the syringes 30 or 32 are engaged with a first plug member 30 with the help of the exteriorly threaded nose portions 32 and 34, a fluid communication is established between interior of the syringes 30, 32 and the aperture 28. The syringes 30 and 32 can be quickly connected and disconnected from the plug member 24 by using internal threads in the plug member 24 and external threads on the nose portions 32 and 34.

The second enlarged portion 20 is similarly provided with a plug 40 that is formed with a threaded internal opening suitable for receipt of a threaded distal end 42 of a vacuum suction tube 44. The plug 40 is formed with a through central opening 46 (FIG. 2) which communicates with an aperture 48 defined in the second enlargement portion 20. A fluid communication is established between the aperture 48 and the vacuum suction tube 44 when the tube is threadably engaged, with the help of the pin 50, to the plug 40.

The aperture 28 communicates with a channel 52 extending through the body 12, terminating in an open tip 54 of the distal end 16. The aperture 48 communicates with a channel 56 (FIGS. 2 and 4) extending through substantially entire length of the body 12 and terminating in the tip 54.

The proximal end 14 of the body 12 is provided with a cap 60 carrying a plurality of pin connectors 62, 64 and 66. The connector 62 carries a monofilament cleaner line 68 extending through the connector pin 62 and the channel 52. An irrigation tube 70 extends through the connector pin 62 and communicates with a channel 71 for delivering cleaning fluid to a treatment site. The pin connector 64 carries a laser tube 72, with the pin connector 64 communicating with central opening 74 (FIG. 4) formed in the body 12. The laser tube 72 surrounds a laser cable 76 adapted for delivery of laser beam to a treatment site through extension of the tube 72 to the tip 54.

The connector pin 66 is normally closed with a cap 78 but can be used for connecting to a tube 80 to deliver a medication or other suitable fluids to the treatment site.

A first up/down switch 84 is mounted on an exterior of the body 12 (FIGS. 1, 2 and 4), the switch 84 being adapted to move up and down the fiber optic cable tip 86, causing it to extend is through an opening 88 formed in the body 12. A second up/down switch 90 is mounted adjacent to the first switch 84 on the exterior of the body 12. The second switch 90 allows to extend or retract the monofilament cleaner 68 from a channel 92 defined through the body 12.

The switches 84 and 90 slide within openings 94 and 96, respectively, formed in the body 12, causing the monofilament cleaner 68 and the optical cable 88 through the tip 54 of the body 12. The monofilament cleaner is moved outwardly from the tip 54 when the treatment site needs to be cleaned and decay removed, in conjunction with the irrigation of the site with a fluid delivered through a tube 70. The fiberoptic cable 88 is extended through the tip 54 when the doctor needs to inspect the treatment site before or during a medical procedure.

A channel 110 formed in the body of the tool 10 is left spare. The channel 110 is normally closed and can be utilized for connection of additional syringes, tubes for delivery of medication, insertion of microforceps for removal of foreign bodies, or other necessary means to the treatment site.

It is envisioned that microforceps can be used with the instrument of the present invention in order to grasp small foreign bodies and retrieve them through the instrument. The foreign bodies can be placed in front of laser beam in a safe location and disk fragments can be destroyed, thus causing a minimum of surgical trauma.

Figure 5:
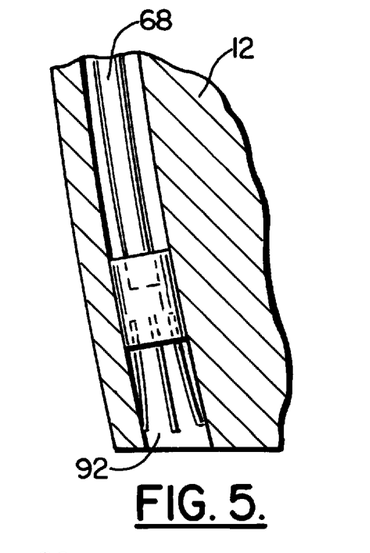
FIG. 5 is a detail view showing position of a monofilament cleaner that forms a part of the medical tool in accordance with the present invention.
Figure 6:
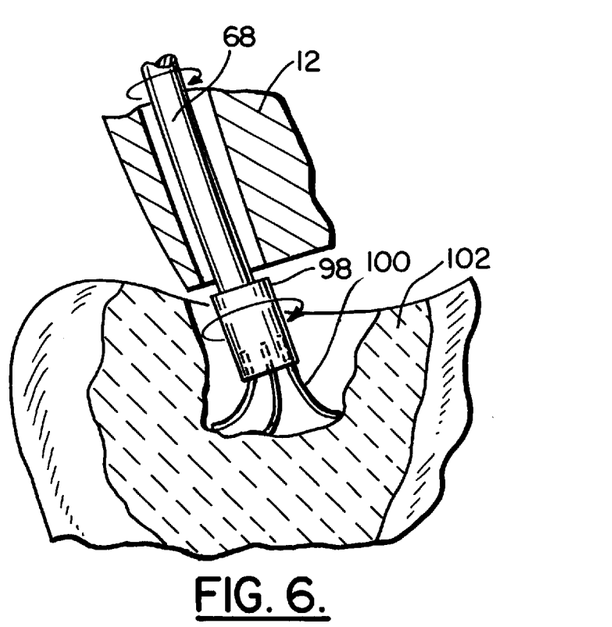
FIG. 6 is a detail view illustrating the use of the monofilament cleaner in repairing a bone structure.

Turning now to FIGS. 5 and 6, the operation of the tool 10 will be discussed in more detail. The monofilament cleaner 68 normally rests within the channel 92, within the limits of the body 12. When cleaning of a treatment site needs to be performed, for example, site of a damaged bone structure, the filament cleaner 68 is extended from the body 12, as shown in FIG. 6, such that a filament carrier 98 and the monofilament fibers 100 move out of the channel 92 outside of the body 12. Torque is imparted on the cleaner body 68, rotating the fibers 100 at a considerable speed, and forcing the fibers 100 into a contact with the damaged bone structure or a decayed tooth structure.

High speed rotation of the fibers 100 causes soft damaged tissue to become loose and separate from the bone structure which is shown schematically at 102 in FIG. 6. The separated particles of the bone are removed from the treatment site with the help of a fluid delivered through the irrigation tube 70 and a suction force established with the tube 104 and acting on the treatment site through the channels 48 and 56. In this manner, the irrigation fluid, as well as the loose particles of the damaged tissue can be removed from the treatment site, leaving the bone area 102 clean and ready for subsequent treatment steps.

Figure 7:
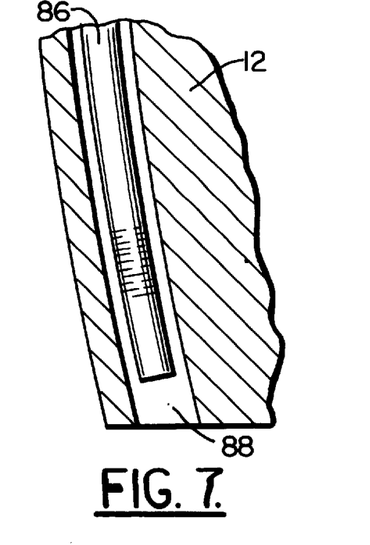
FIG. 7 is a detail view of a fiberoptic television camera tip that forms a part of the tool in accordance with the present invention.
Figure 8:
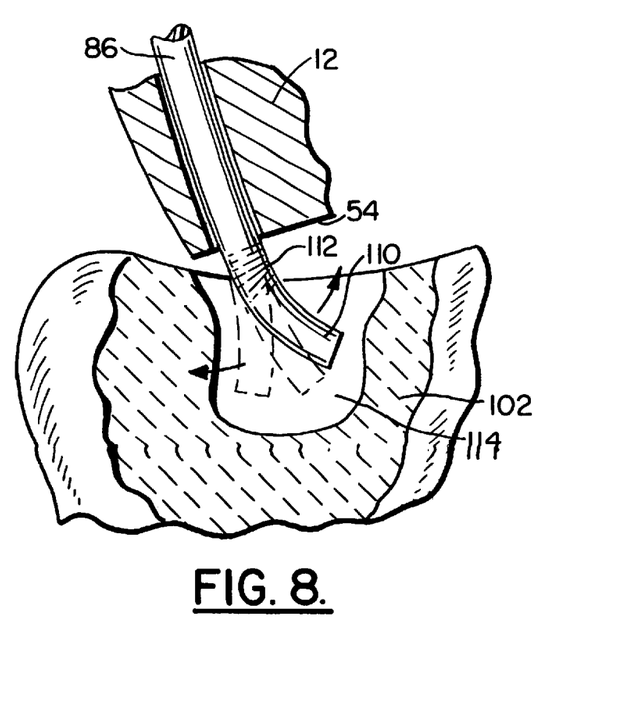
FIG. 8 is a detail view showing extension of the tip of the fiberoptic cable into a close proximity with the treatment site.

FIGS. 7 and 8 illustrate in more detail the manner of using a television cable which forms a part of the tool 10. As shown in FIG. 7, the television cable 86 is normally retained in the channel 88 within the body 12. When it is necessary to perform inspection of the site of treatment, the switch 84 is manually operated, causing the cable 86 to move outwardly from the tip 54 of the body 12 and extend, to a discrete distance, from the opening formed in the tip 54. The most distal end 110 of the cable 86 oscillates right and left, forward and backward in response to an electrical signal delivered through the cable 86.

By moving the most distal end 110 in different directions, thanks to a flexible connector 112, an inspection of a site 114 in the bone structure 102 can be performed. Once the inspection is completed, in response to a control command sent through the cable 86, the distal end 110 is withdrawn from the site 114 back into the channel 88.

The extension and withdrawal of the portion of the fiber optic cable 86 can be done at any time during the treatment procedure either for the purpose of evaluation of the damage to the bone structure 102, or to evaluate the success of cleaning of the site 114, or subsequent to treatment, to evaluate whether any hidden damage, cracks or imperfections remain in the treated bone structure (tooth).

Figure 10:
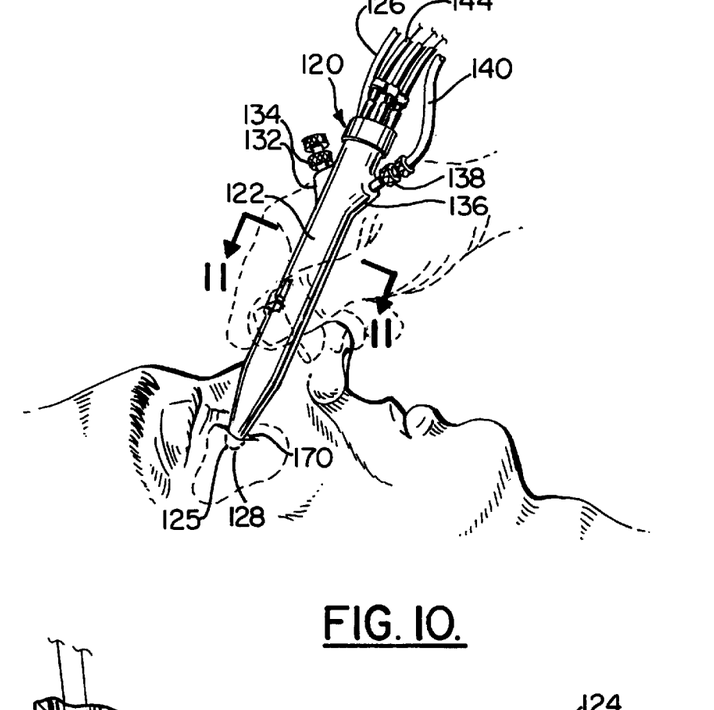
FIG. 10 is a perspective view showing the use of the medical tool of the present invention in treatment of sinuses.
Figure 11:
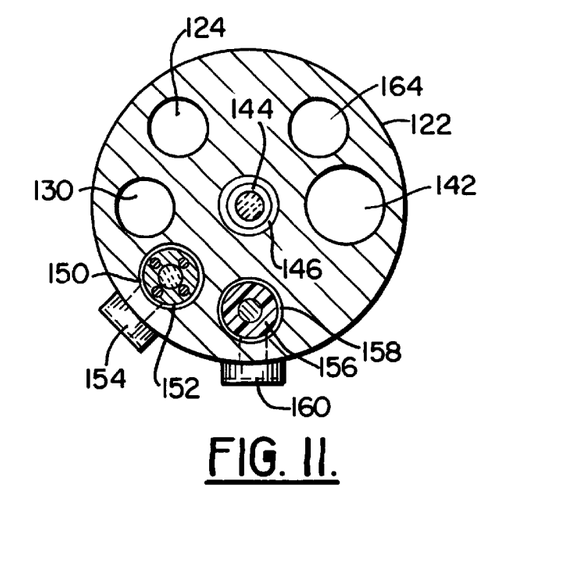
FIG. 11 is a cross-sectional view taken along lines 11—11 in FIG. 10.
Figure 12:
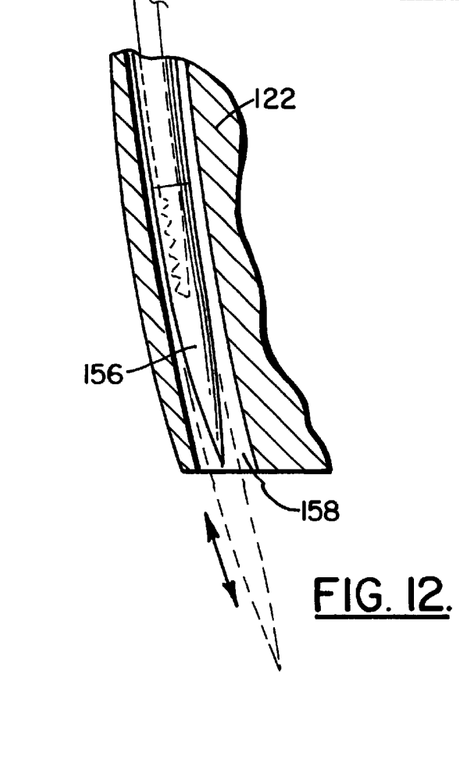
FIG. 12 is a detail view showing a pinpoint bipolar cautery forming a part of the tool shown in FIG. 10.

Turning now to FIGS. 10–12, a tool 120 is illustrated in use for treatment of sinuses. The tool 120, similar to the tool 10, comprises an elongated, generally cylindrical body 122 provided with a plurality of channels extending through the body. A channel 124 is adapted for retaining an irrigation tube 126 therein. The irrigation tube 126 delivers a fluid to a treatment site 128 during the use of the device 120. A channel 130 is in fluid communication with the first enlarged portion 132 adapted for connecting a syringe with a medication to a normally closed end of the channel 130.

A suitable pin 134, similar in structure to the pin 22 is secured at one end of the first enlargement portion 132. The second enlargement portion 136 carries a pin 138 that is adapted for engagement with a vacuum tube 140 by threadably engaging a connector pin on the end of the tube 140 with the pin 138. The tube 140 communicates with a channel 142 creating a suction force in the channel 142 and allowing to evacuate fluids and find tissue particles from the treatment site 128. A laser cable 144 extends through a central channel 146 formed in the body 122, the laser cable 144 delivering a light beam to the treatment site to help treat the damaged area.

A television fiberoptic cable 150 extends through a channel 152 formed in the body 122, allowing the doctor to inspect the treatment site during the treatment procedure. An up/down switch 154 slidably engaged with the wall of the body 122 allows to extend and retract the fiberoptic cable 150, similarly to the cable 86 of the tool 10.

A pinpoint bipolar cautery 156 extends through a channel 158 and is caused to move in and out of the body 122 in response to activation of an up/down switch 160 slidably engaged with the wall of the body 122. The cautery 156 normally rests in the channel 156, as shown in solid line in FIG. 12, and can be moved outwardly from the body 122 in the direction shown in phantom lines in FIG. 12 during a treatment procedure.

The cautery 156 is adapted to destroy dead or damaged tissue in the treatment site 128, so as to prevent the spread of infection, help seal blood vessels and the like. When electrical current is delivered through the cautery 156, it is transmitted through the body of the cautery to the damaged tissue, burning the unwanted tissue with a pinpoint accuracy.

An additional channel 164 formed in the body 122 is left intentionally spare, with a view to using the channel 164 by either connecting additional syringes or tubes for delivery of microforceps, medication or other treatment means to the site 128.

As can be seen in FIG. 10, an incision 170 is made in the body of the patient, and a tip 125 of the body 122 is introduced through the incision to the treatment site 128. The incision 170 can be made of much smaller dimensions, due to a reduced diameter of the tip 125, as compared with conventional tools and methods. By holding the tool 120, as shown phantom line in FIG. 10, a physician can perform the necessary examination of the sinuses of the patient, manipulate television camera, extension of the cautery and removal of the unwanted tissue.

Figures 13, 14:
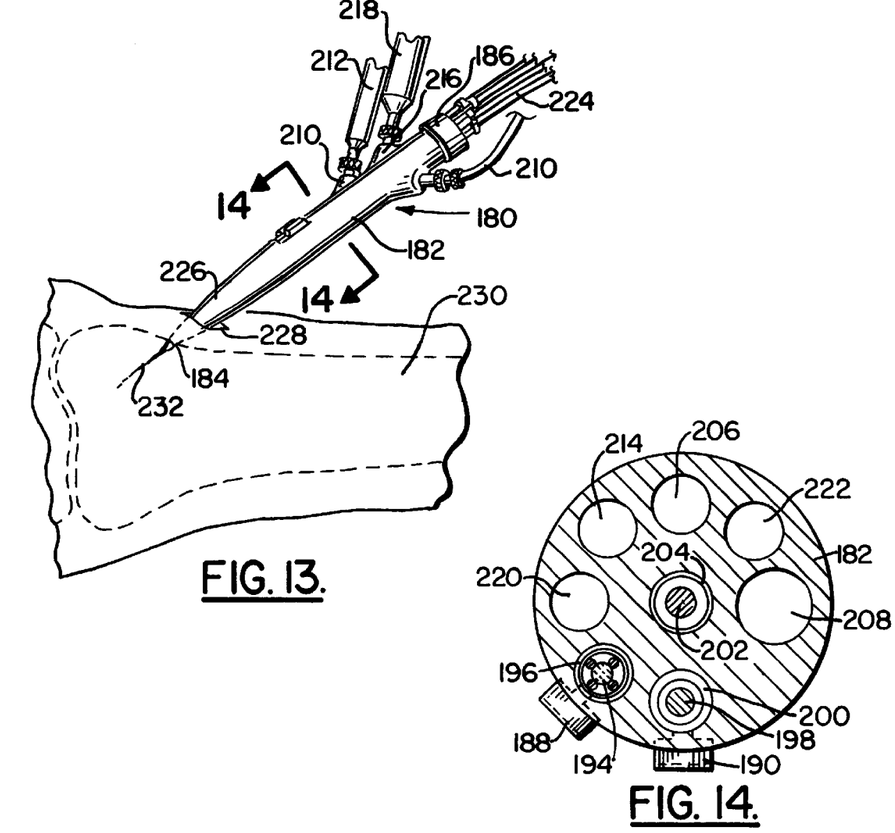
FIG. 13 is a perspective view showing the use of the tool in accordance with the present invention during an orthopaedic/neurosurgical procedure.
FIG. 14 is a cross-sectional view taken along lines 14—14 of FIG. 13.

FIGS. 13 and 14 illustrate a tool 180 particularly adapted for use in orthopaedic procedures. The tool 180 comprises a generally cylindrical body 182 provided with a plurality of channels passing through the body. Similarly to the embodiments shown in FIGS. 1–12, the body 182 has an open tip 194 formed in a distal end of the body 192 and a cap 186 secured on the proximate end of the body 182. A pair of up/down switches 188 and 190 are mounted in slidable engagement with the body 182 and are adapted to extend and retract a television camera cable and a pinpoint bipolar cautery, respectively. The switch 198 is in operational communication with a television cable 194 extending through a channel 196 formed in the body 182. A bipolar cautery cable 198 extends in the channel 200 and can be extended outwardly from the tip 194 or be retracted into the body 182 upon a signal transmitted by the switch 190.

A laser cable 202 extends through the central channel 204 for delivery of a high power light beam to the treatment site. An irrigation channel 206 delivers fluid to the treatment site to help clean the site and remove unwanted or damaged tissue. A vacuum channel 208 is connected to the vacuum tube 210 for evacuating the fluids and particles of damaged bone or tissue from the treatment site.

The tool body 192 is provided with a first enlarged portion 210 that is adapted for connection to a syringe, or a vial 212 containing a pain medication for delivering the medication through the channel 214 formed in the body 182. A second enlarged portion 216 is adapted for connection to a syringe, or vial 218 containing bone cement or other similar adhesive substance for delivering the substance through a channel 220 to the treatment site. A spare channel 222 is formed in the body 192 in case other medications or treatment agents need to be used during an orthopaedic procedure.

The television cable 194, the cautery wire 198, and an irrigation tube 224 extend through corresponding openings formed in the cap 196, as shown in FIG. 13. As further shown in FIG. 13, the orthopaedic tool 180 is held in the hand of a doctor, similarly to a pen, allowing the doctor to manipulate the switches 188 an 190 for inspecting the damaged site and for delivering a cauterization wire 198 closer to the damaged area.

When in use, a reduced diameter distal end 226 of the tool 180 is inserted through an incision 228 formed in the soft tissue of the patient, in immediate proximity to a bone 230, particularly to a damaged area 232, where the treatment is to be performed. By alternatively connecting and disconnecting the various attachments to the tool 180, the doctor can inspect the site of a bone damage by using the television cable 194, deliver a laser beam to the site through the laser cable 202, use cauterization by using the pinpoint cautery 198, and to irrigate and clean the site by using the vacuum tube 210 and the microforceps and the irrigation tube 224.

Pain medication or antibiotic can then be delivered through the syringe or vial 212 in fluid communication with the channel 214, and a strengthening, sealing bone cement can be delivered from a vial or syringe 218 in fluid communication with the channel 220 and, thereby, with the treatment site 232. Preferably, the vacuum channel 208 is formed with a greater diameter in comparison with the channels shown in the embodiments of FIGS. 1–12. The enlarged vacuum channel 208 is needed to successfully evacuate larger particles of bone tissue from the treatment site 232.

Figure 15:
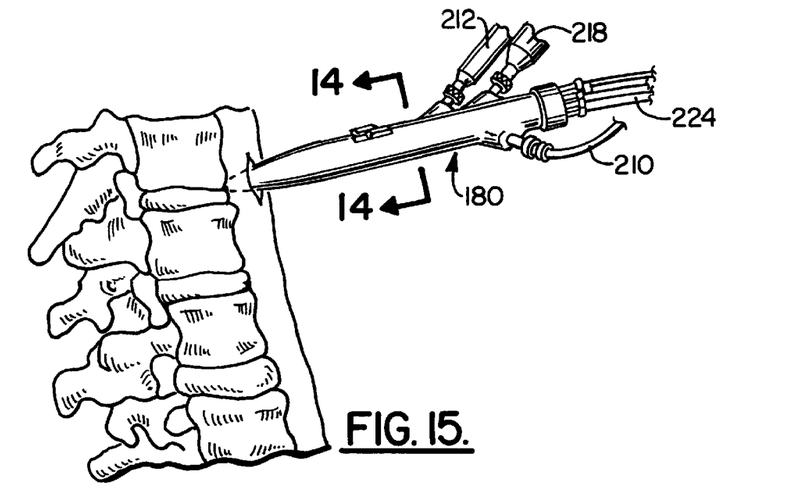
FIG. 15 is a perspective view showing the tool of the present invention in use during a spinal surgery.

FIG. 15 illustrates the use of the tool 180 in relation to a procedure performed on a spinal cord of a patient. In that case, it is preferred that the vial 212 contain an antibiotic liquid, and vial 218 contain a pain medication. The operation of the tool 180 during a spinal surgery would be similar to the operation of the device during an orthopaedic procedure, allowing the surgeon to manipulate the up/down switches 188 and 190 with his thumb, and connecting and disconnecting various attachments to the tool 180 with his other hand, if necessary, or allowing attendant personnel to connect, disconnect syringes 212 and 218.

Figure 16:
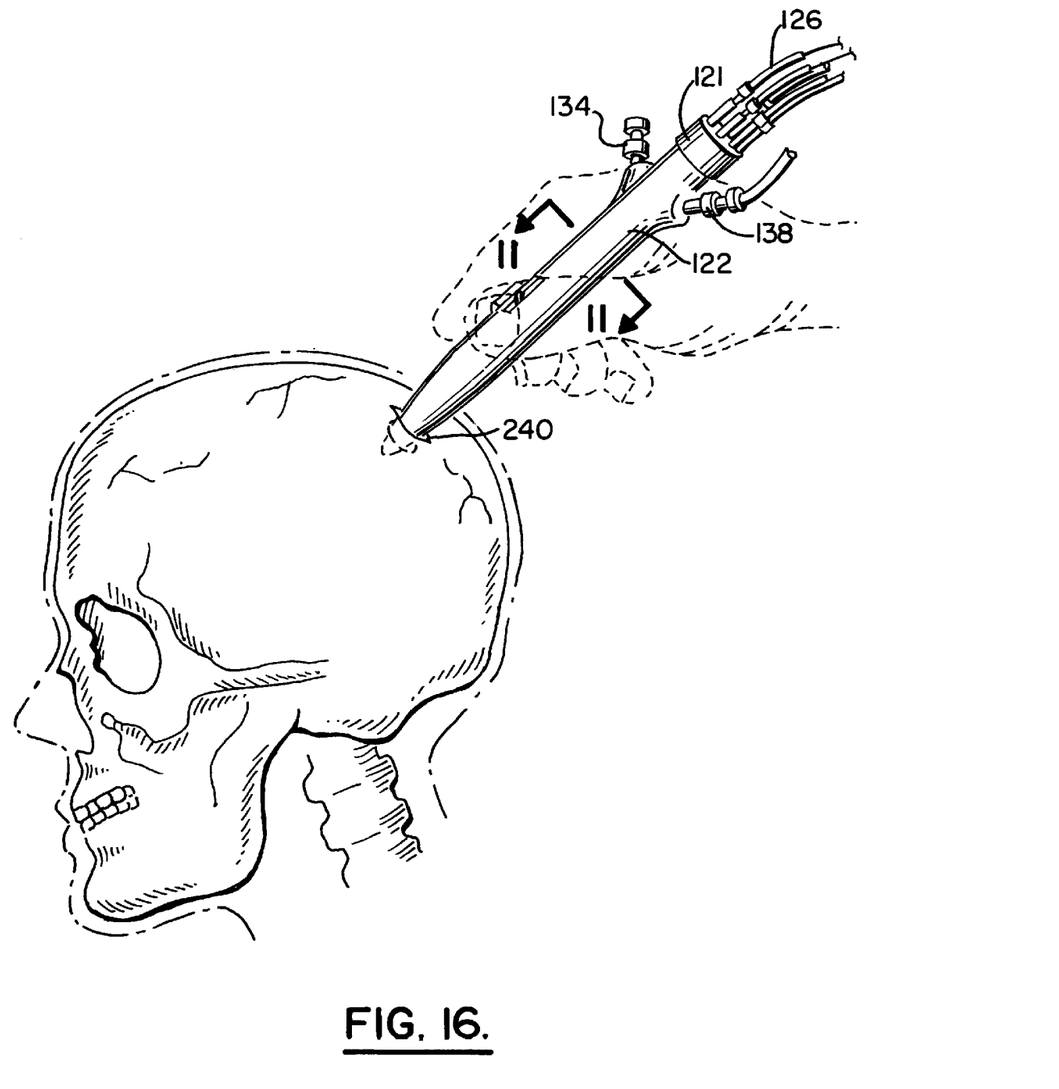
FIG. 16 is a perspective view showing the use of the tool in accordance with the present invention during a neurosurgery.

FIG. 16 illustrates the use of the tool shown in FIG. 10 during a neurosurgery. The tool, as described above, contains a tool body 122 formed with a plurality of channels for delivering medications, irrigation and other necessary fluids to a treatment site 240. The switches 154 and 160 can be manipulated either by an index finger of a surgeon or a thumb of a surgeon, as shown in phantom lines in FIG. 16, similarly to the use of the tool during a sinus operation. The plug connectors 134 and 138 are similarly adapted for connection to a syringe and a vacuum tube, respectively. The cap 121 is similarly formed with a plurality of openings allowing extension of irrigation, laser, pinpoint bipolar cautery and television cable conduits from the tool 120 for connection to external devices.

Figure 9:
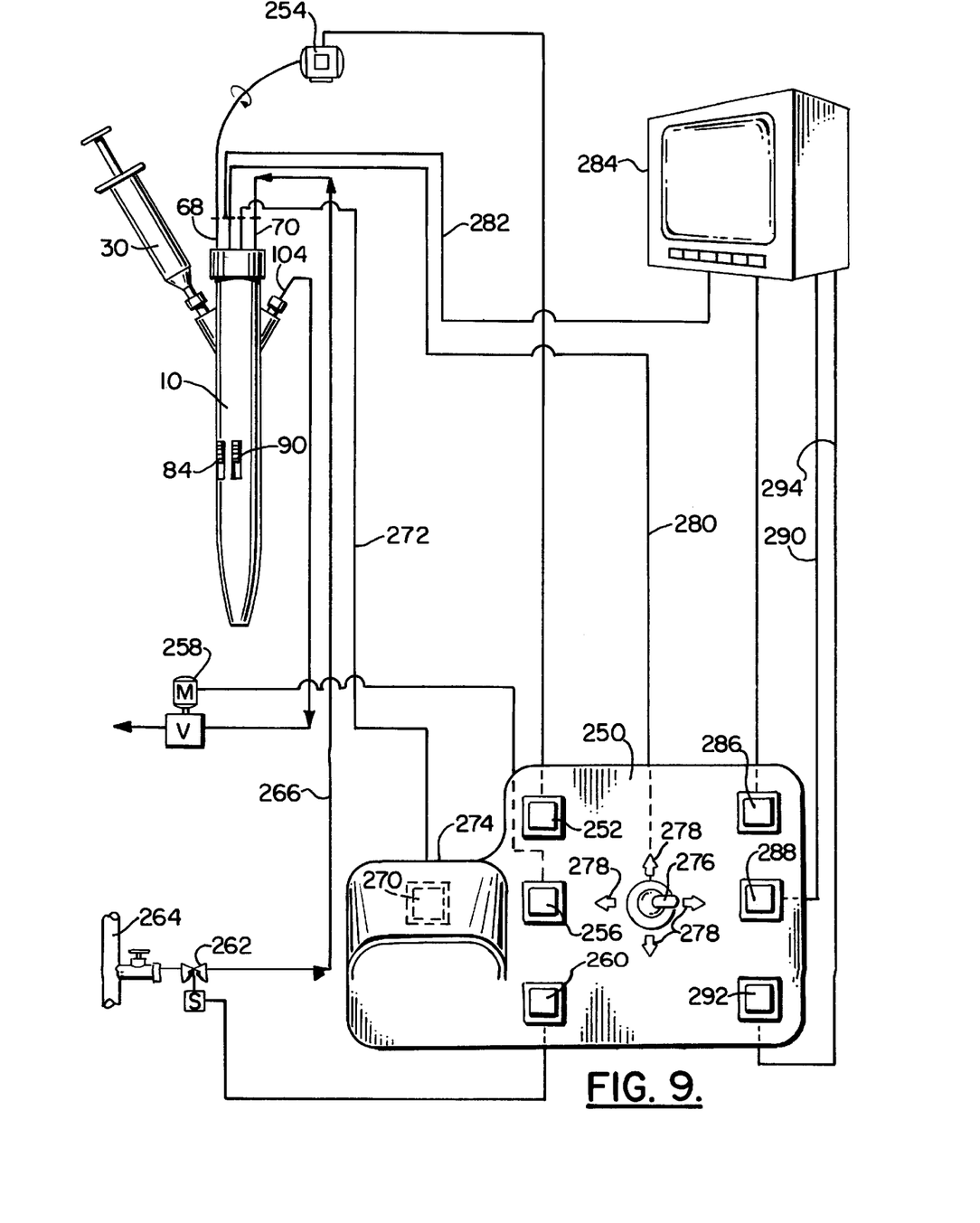
FIG. 9 is a schematic view of the apparatus in accordance with the present invention.

Turning now to FIG. 9, the operation of the tools shown in FIGS. 1–8 and 10–16 will be described with reference to a tool 10. It is to be understood that the tools 120 and 180 are similar in operation, with minor modifications for delivery of different types of medications, irrigation or treatment fluids to a damaged site.

As shown in FIG. 9, the apparatus of the present invention comprises the tool 10 connected by a plurality of electrical and fluid lines to the control and monitoring equipment. A foot pedal 250 is provided for use by a surgeon or dentist. The foot pedal 250 has a plurality of switches for controlling a magnifying picture of a television camera, light, magnification and the like.

A switch 252 is an on/of switch designed to control a monofilament cleaner 68 by sending a signal to a motor 254 that imparts rotational force on the cleaner body and transmits it through the filaments 100. A switch 256 controls operation of a vacuum motor 258, adapted to establish a vacuum in the suction line 104. A switch 260 is connected through a solenoid valve 262 to a water line 264 which, in turn, is connected by suitable tubing 266 to an irrigation tube 70.

An on/off switch 270 controls operation of a laser through appropriate wiring 272 delivering a signal to the cable 76. A cover 274 is provided for protecting the switch 270 and preventing accidental energizing of the laser beam when not required by the surgeon or dentist.

Occupying a central position on the foot pedal 250 is a control pad 276 with directional arrows 278 for controlling movement of a fiber optic cable during examination of the damaged site. By moving foot in different directions, as shown by arrows 278, the doctor can transmit the signal through corresponding wiring 280 to the fiber optic cable, moving the tip 110 of the cable in different directions, as shown in FIG. 8. The fiber optic cable is also operationally connected through appropriate wiring 282 to a television monitor 284 positioned within a visual distance of the working physician. The monitor 284 is also controlled by an on/off switch 286 mounted on the foot pedal 250. A switch 288 is connected to a multiple light source control line 290 on the monitor 284, and a control button 292 on the foot pedal 250 is connected by a suitable wiring 294 to the television monitor 284. The switch 292 allows the physician to magnify the image received by the fiber optic cable 268 of the damaged site and display a magnified image on the monitor 284 with various light sources.

By switching the control buttons on the foot pedal 250, in conjunction with the up/down switches 84 and 90, the treating doctor can inspect the damaged site, affect cleaning of the site and removal of the damaged tissue by using either laser, a monofilament cleaner, or a bipolar cautery, remove the unwanted tissue by irrigating the site and establishing a vacuum connection to remove the unwanted tissue from the treatment site and deliver a medication, bone cement or other necessary fluids to stabilize and repair the bone structure. If desired, a follow up examination, after the cement has set, can be similarly conducted through the use of the fiber optic cable and the TV monitor, to make sure that all areas are properly sealed and protected.

A pain killer medication can be delivered during the surgery by using the syringes 30, 32. The syringe 32, as described above, can deliver multiple treatment fluids to the treatment site by using the two-chamber construction and two plungers. The use of laser and pinpoint cautery allows the sealing of the blood vessels and prevents excessive bleeding.

Additionally, the physician can deliver various diagnostic colored or staining liquid to the repair site by using the same syringe connector and a different type of syringe. It is possible to dye the tissue in the damaged area with, for example, fluorescein stain to highlight the damaged tissue prior to the examination by the television camera. By lowering or raising the intensity of various colors and sources of light, it is possible to better observe the bone structure and make a better examination of the damaged area.

It is also possible to illuminate the treatment site with different colors, for example the switch 288 can be used to deliver a cobalt blue, or infrared, or green light to the site to enhance the pathology of the bone. The cleaning of the wound can be made with hydrogen peroxide or other similar liquids delivered through the irrigation line, in conjunction or separately from the water connection.

The device of the present invention allows to use various types of sealers, in addition to the bone cement. For example, an epoxy, a thermal plastic resin and other fast curing substances can be used for repair of the damaged bone structure. In addition, particularly in use during dental procedures, a cavity dissolving solution can be injected into a tooth cavity, and a solution to highlight residual dental caries as well as a sealer, for example using the syringe 32.

By using the system of the present invention, the surgeon can perform the exploratory and treatment procedures in several minutes, as opposed to 30 or more minutes usually required for such procedures. The use of the television camera with a possibility to magnify the damaged area facilitates better results and allows more complete sealing and protection of the damaged bone structure then with the naked eye.

Many changes and modifications can be made in the apparatus of the present invention without departing from the spirit thereof. I, therefore, pray that my rights to the present invention be limited only by the scope of the appended claims.

I claim:

1. An apparatus for repairing damaged bone structure, comprising:
    a hand-held instrument having a generally cylindrical body with a plurality of channels formed in said body;
    a means for connecting said body to a laser beam generating source;
    a means for connecting said body to a television monitor;
    a means for connecting said body to a source of fluid to be delivered to a site of damaged bone structure;
    a means for connecting said body to a vacuum creating device, so as to evacuate unwanted solid particles and fluids from the site of damaged bone structure;
    a means for controlling a connection between said body and said television monitor; and
    a means for connecting said body to a source of medication, said means comprising a normally closed pin connector having internal threads for threadable engagement with the medication source, said pin connector being secured on an exterior of said body.

2. An apparatus for repairing damaged bone structure, comprising:
    a hand-held instrument having a generally cylindrical body with a plurality of channels formed in said body;
    a means for connecting said body to a laser beam generating source;
    a means for connecting said body to a television monitor;
    a means for connecting said body to a source of fluid to be delivered to a site of damaged bone structure;
    a means for connecting said body to a vacuum creating device, so as to evacuate unwanted solid particles and fluids from the site of damaged bone structure;
    a means for controlling a connection between said body and said television monitor; and
    a means for connecting said body to a source of bone sealant, said means comprising a normally closed attachment pin adapted for detachable engagement with the source of the bone sealant, said attachment pin being secured on an exterior of said body.

3. An apparatus for repairing damaged bone structure, comprising:
    a hand-held instrument having a generally cylindrical body with a plurality of channels formed in said body, one of said channels being adapted for retaining a fiber optic cable connected to the television monitor, said cable being extendable upon demand through an open distal end of the body to allow inspection of the damaged bone site, a second of said channels being adapted for housing a laser cable operationally connected to a laser beam generating source and to a control switch for energizing said laser beam operating source;
    a means for connecting said body to a laser beam generating source;
    a means for connecting said body to a television monitor;
    a means for connecting said body to a source of fluid to be delivered to a site of damaged bone structure;
    a means for connecting said body to a vacuum creating device, so as to evacuate unwanted solid particles and fluids from the site of damaged bone structure;
    a means for controlling a connection between said body and said television monitor;
    a control pad for monitoring direction of said fiber optic cable, intensity and color of light transmitted to the site of the damaged bone structure, magnification of an area examined with said television monitor and direction of a laser beam, said control pad further comprising a means for transmitting a control signal to said fluid source and establishing a fluid connection between said body and a source of fluid.

4. An apparatus for repairing damaged bone structure, comprising:
    a hand-held instrument having a generally cylindrical body with a plurality of channels formed in said body;
    a means for connecting said body to a laser beam generating source;
    a means for connecting said body to a television monitor;
    a means for connecting said body to a source of fluid to be delivered to a site of damaged bone structure;
    a means for connecting said body to a vacuum creating device, so as to evacuate unwanted solid particles and fluids from the site of damaged bone structure;
    a means for separating unwanted damaged tissue from remainder of a bone structure and delivering the unwanted tissue to an exterior of said body;
    a means for connecting said body to a source of medication, comprising a normally closed pin connector having internal threads for threadable engagement with a source of medication, said pin connector being secured on an exterior of said body; and a control pad for monitoring operation of said connection means mounted in operational relationship to said body.

5. An apparatus for repairing damaged bone structure, comprising:

a hand-held instrument having a generally cylindrical body with a plurality of channels formed in said body;

a means for connecting said body to a laser beam generating source;

a means for connecting said body to a television monitor;

a means for connecting said body to a source of fluid to be delivered to a site of damaged bone structure;

a means for connecting said body to a vacuum creating device, so as to evacuate unwanted solid particles and fluids from the site of damaged bone structure;

a means for separating unwanted damaged tissue from remainder of a bone structure and delivering the unwanted tissue to an exterior of said body;

a means for connecting said body to a source of medication;

a control pad for monitoring operation of said connection means mounted in operational relationship to said body; and a means for connecting said body to a source of a bone sealant, said connecting means comprising a normally closed attachment pin adapted for detachable engagement with the source of the bone sealant, said attachment pin being secured on an exterior of said body.

* * * * *